(12) United States Patent
Orth et al.

(10) Patent No.: US 7,796,811 B2
(45) Date of Patent: Sep. 14, 2010

(54) METHOD FOR OBTAINING A POSITION MATCH OF 3D DATA SETS IN A DENTAL CAD/CAM SYSTEM

(75) Inventors: Ulrich Orth, Heppenheim (DE); Volker Wedler, Hirschberg (DE)

(73) Assignee: Sirona Dental Systems GmbH, Benshiem (DE)

( * ) Notice: Subject to any disclaimer, the term of this patent is extended or adjusted under 35 U.S.C. 154(b) by 981 days.

(21) Appl. No.: 11/368,535

(22) Filed: Mar. 7, 2006

(65) Prior Publication Data

US 2006/0204078 A1 Sep. 14, 2006

Related U.S. Application Data

(60) Provisional application No. 60/749,612, filed on Dec. 13, 2005.

(30) Foreign Application Priority Data

Mar. 8, 2005 (DE) ........................ 10 2005 011 066

(51) Int. Cl.
*G06K 9/00* (2006.01)
(52) U.S. Cl. ...................................... 382/154
(58) Field of Classification Search ................ 382/154; 345/419–427
See application file for complete search history.

(56) References Cited

U.S. PATENT DOCUMENTS 4,183,139 A  1/1980  Tanaka ........................... 32/19

(Continued)

FOREIGN PATENT DOCUMENTS

| DE | 196 42 247 C1 | 1/1998 |
| EP | 1 252 867 | 10/2002 |
| WO | 2004/044787 A2 | 5/2004 |
| WO | 2005/004742 A1 | 1/2005 |

OTHER PUBLICATIONS

European Search Report issued on Jun. 22, 2006, along with English language translation.

(Continued)

*Primary Examiner*—Vu Le
*Assistant Examiner*—Alex Liew
(74) *Attorney, Agent, or Firm*—Fitzpatrick, Cella, Harper & Scinto (57) ABSTRACT

Disclosed is a method for designing tooth surfaces of a digital dental prosthetic item existing as a 3D data set using a first 3D model of a preparation site and/or of a dental prosthetic item and a second 3D model, which second model comprises regions which match some regions on the first 3D model and regions which differ from other regions of the first 3D model, the non-matching regions containing some of the surface information required for the dental prosthetic item, wherein at least three pairs (P1, P2, P3) of points (P11, P12; P21, P22; P31, P32) corresponding to each other are selected on the matching region on the first 3D model (A) and the second 3D model (A'), that the positional correlation of the second 3D model with reference to the first 3D model is determined with reference to the at least three pairs (P1, P2, P3), and that portions of the non-matching regions of the first and second 3D models are implemented for designing the tooth surface of the dental prosthetic item taking into consideration the positional correlation of these models relative to each other.

15 Claims, 4 Drawing Sheets

U.S. PATENT DOCUMENTS

| | | | | |
|---|---|---|---|---|
| 4,734,034 | A | | 3/1988 | Maness et al. ............... 433/68 |
| 4,742,464 | A | | 5/1988 | Duret et al. ................. 364/474 |
| 4,766,704 | A | | 8/1988 | Brandestini et al. .......... 51/327 |
| 4,856,993 | A | | 8/1989 | Maness et al. ............... 433/68 |
| 4,937,928 | A | | 7/1990 | Van der Zel ............... 29/896.1 |
| 5,027,281 | A | * | 6/1991 | Rekow et al. ............... 700/182 |
| 5,273,429 | A | | 12/1993 | Rekow et al. ............... 433/215 |
| 5,604,817 | A | | 2/1997 | Massen et al. ............. 382/120 |
| 5,691,905 | A | | 11/1997 | Dehoff et al. ................ 700/98 |
| 6,152,731 | A | | 11/2000 | Jordan et al. ................. 433/69 |
| 6,163,337 | A | * | 12/2000 | Azuma et al. ................ 348/43 |
| 6,174,168 | B1 | | 1/2001 | Dehoff et al. ............ 433/202.1 |
| 6,334,853 | B1 | | 1/2002 | Kopelman et al. .......... 600/590 |
| 6,614,429 | B1 | * | 9/2003 | Zhang et al. ................ 345/420 |
| 6,621,491 | B1 | * | 9/2003 | Baumrind et al. ........... 345/419 |
| 6,821,462 | B2 | | 11/2004 | Schulman et al. ............. 264/16 |
| 7,086,863 | B2 | | 8/2006 | Van der Zel ............... 433/223 |
| 7,399,181 | B2 | | 7/2008 | Weber et al. ................. 433/29 |
| 2002/0094509 | A1 | | 7/2002 | Durbin et al. ............... 433/213 |
| 2004/0172150 | A1 | | 9/2004 | Perot et al. .................... 700/98 |
| 2006/0008776 | A1 | | 1/2006 | Orth et al. ................... 433/215 |
| 2006/0063135 | A1 | | 3/2006 | Mehl ........................... 433/223 |
| 2006/0212154 | A1 | | 9/2006 | Von Schroeter et al. ..... 700/118 |

OTHER PUBLICATIONS

Communication from the German Patent Office issued on Apr. 18, 2006, along with English-Language translation.

* cited by examiner

METHOD FOR OBTAINING A POSITION MATCH OF 3D DATA SETS IN A DENTAL CAD/CAM SYSTEM

CROSS-REFERENCE TO RELATED APPLICATIONS

This application claims the priority of German Application No. 10 2005 011 066.5, filed Mar. 8, 2005, and is related to U.S. Provisional Application No. 60/749,612, filed Dec. 13, 2005, the priority of which is hereby claimed.

TECHNICAL FIELD

This invention relates to part of a process for the manufacture of dental prosthetic items in a dental CAD system.

In the dental CAD/CAM system "CEREC" (registered trademark of Sirona Dental Systems GmbH, Germany), the operator performs a 3D scan of a prepared tooth and its adjacent teeth, from which scan a data representation of the 3D model of the region scanned is produced in the memory unit of a computer and displayed.

DESCRIPTION OF THE RELATED ART

In order to copy, say, the chewing surface of a tooth prior to preparation, the tooth can be scanned prior to preparation, together with the adjacent teeth, and a corresponding 3D model can then be computed.

Another variant comprises the scanning of an impression of the opposite jaw, in order to achieve an optimum fit of the dental prosthetic item on said opposite jaw.

In order to be able to use the information of the unprepared tooth or the impression of the opposite jaw, it is necessary to achieve a sufficiently exact geometric alignment of the corresponding models to the model of the prepared tooth. The information that makes such alignment possible must therefore be contained in the models.

The use of the surface of the adjacent teeth, with no change in the surface between the scans, is known in the prior art. This normally takes place automatically via the software, by means of which regions of the 3D data set corresponding to each other are sought and found.

There are cases in which this automatic process fails, due, for example, to the poor quality of the scans, too few unaltered parts of the 3D models, or interfering image components such as cofferdams or rolls of cellulose wadding.

Despite this, and in order to be able to use this information either from the scans prior to preparation or from the opposite jaw, the position match of the models must be obtained in a different way.

OBJECTS AND SUMMARY OF THE INVENTION

The invention relates to a method for designing dental surfaces for a digital dental prosthetic item existing as a 3D data set by means of a first 3D model of a preparation site and/or of a yet to be milled dental prosthetic item and a second 3D model, which second model includes regions which match some regions on the first 3D model and regions which differ from other regions of said first 3D model. The non-matching regions contain some of the surface information required for the dental prosthetic item.

At least three pairs of points corresponding to each other are selected on the matching region on the first 3D model A and the second 3D model A', and the positional correlation of said second 3D model (A') relative to said first 3D model (A) is determined with reference to the at least three pairs of points.

The portions of the non-matching regions of the first 3D model (A) and of the second 3D model (A') are implemented for designing the tooth surface of the dental prosthetic item taking into consideration the positional correlation of these 3D models relative to each other.

The 3D model (A) can, for example, comprise a digital representation of a prepared tooth with its adjacent teeth and the 3D model (A') a digital representation in approximately the same preparation site of an impression of the opposite jaw. The matching regions would then comprise at least portions of the occlusal surfaces of the adjacent teeth of the first 3D model (A) and the opposite occlusal surfaces of the opposing teeth in the opposite jaw of the second 3D model (A'). The non-matching regions would then comprise at least portions of the surface of the prepared tooth in the first 3D model (A) and the occlusal surface of the opposing tooth in the second 3D model (A') and could be implemented for designing the tooth surface of the dental prosthetic item for the prepared tooth.

The alignment of points and regions on the second 3D model (A') and the first 3D model (A) by way of the positional correlation is known in the prior art.

The alignment of the points is achieved by intervention by the operator.

In order to achieve unambiguous determination of the positional correlation of the first 3D model (A) relative to the second 3D model (A'), at least three pairs of points in the matching regions must be selected by the operator, and these three pairs of points may not be in line.

Furthermore, the invention relates to a method for designing dental surfaces of a digital dental prosthetic item existing as a 3D data set by means of a first 3D model (A) of a preparation site and/or a dental prosthetic item yet to be milled and a second 3D model (A'), which second model (A') has regions matching some regions of the first 3D model (A) and regions which do not match other regions of the first 3D model (A), which non-matching regions contain some of the surface information required for the dental prosthetic item. A plurality of points forming a region of the surface is selected from the matching region on the first 3D model (A) and the second 3D model (A'), and the positional correlation of said second 3D model (A') relative to the first 3D model (A) is determined with reference to the plurality of points in said region. The portions of the non-matching regions of the first 3D model (A) and of the second 3D model (A') are used for designing the tooth surface of the dental prosthetic item taking into consideration the positional correlation of these 3D models relative to each other.

Advantageously, a plurality of regions having a plurality of points can be determined.

In a development of the invention, the sum of the distances between the established points on the first 3D model (A) and the established points on the second 3D model (A') or between the points in the matching regions is minimized for the determination of the positional correlation.

When the points are selected by the operator small deviations from the actually matching points may occur. The sum of the distances of the selected pairs of points is minimized in order to keep this error down. Assuming that the error occurring when the points are selected by the operator is approximately constant, the actual positional correlation will be determine more accurately as the number of selected pairs of points is increased.

Furthermore, the invention embraces a method for designing dental surfaces of a digital dental prosthetic item existing as a 3D data set by means of a first 3D model of a preparation site and/or of a dental prosthetic item yet to be milled and a second 3D model, which second model has regions matching some regions on the first 3D model and other regions which do not match other regions on the first 3D model. The non-matching regions contain some of the surface information required for the dental prosthetic item. A pair of points corresponding to each other is selected on the matching region on said first 3D model and said second 3D model, and the second 3D model is moved in the display so as to coincide with the first 3D model at this point. The second 3D model (A') can then be adjusted, via input means, relatively to the first 3D model (A) about the at least one point, and a positional correlation is determined with reference to an adjusted position. The portions of the non-matching regions of the first and second 3D models are then implemented for designing the tooth surface of the dental prosthetic item taking into consideration the positional correlation of said 3D models relative to one another. The selection of the point and the adjustment are performed by the operator.

The second 3D model is then manipulated around the selected coincidence point until the first 3D model matches the second 3D model at as many points as possible. The total adjustment can then be implemented to determine the positional correlation.

According to the invention, a first transformation is performed with reference to the established positional correlation.

It is possible to ascertain the first transformation from the positional correlation, and when the first transformation has been carried out, the second 3D model can be moved to coincide with the first 3D model.

In a particularly advantageous development, those regions which, after execution of the first transformation, show a smaller difference in height than a specified maximum value between the first 3D model and the second 3D model are used as the basis for finding an additional positional correlation.

That is to say, those regions which show a greater difference in height than the maximum value are not implemented for determination of an additional positional correlation. In this way, pairs of points inaccurately selected by the operator are screened out.

A second transformation is advantageously performed with reference to said additional positional correlation.

After execution of the first transformation, a second transformation is thus carried out in order to make the second 3D model coincide with the first 3D model even more accurately.

BRIEF DESCRIPTION OF THE DRAWINGS

Exemplary embodiments of the invention are illustrated in the drawings, in which:

FIG. 3b illustrates the rotation of the coordinate system K2' of FIG. 3a;

DETAILED DESCRIPTION OF AN EXEMPLARY EMBODIMENT OF THE INVENTION

Figure 1:
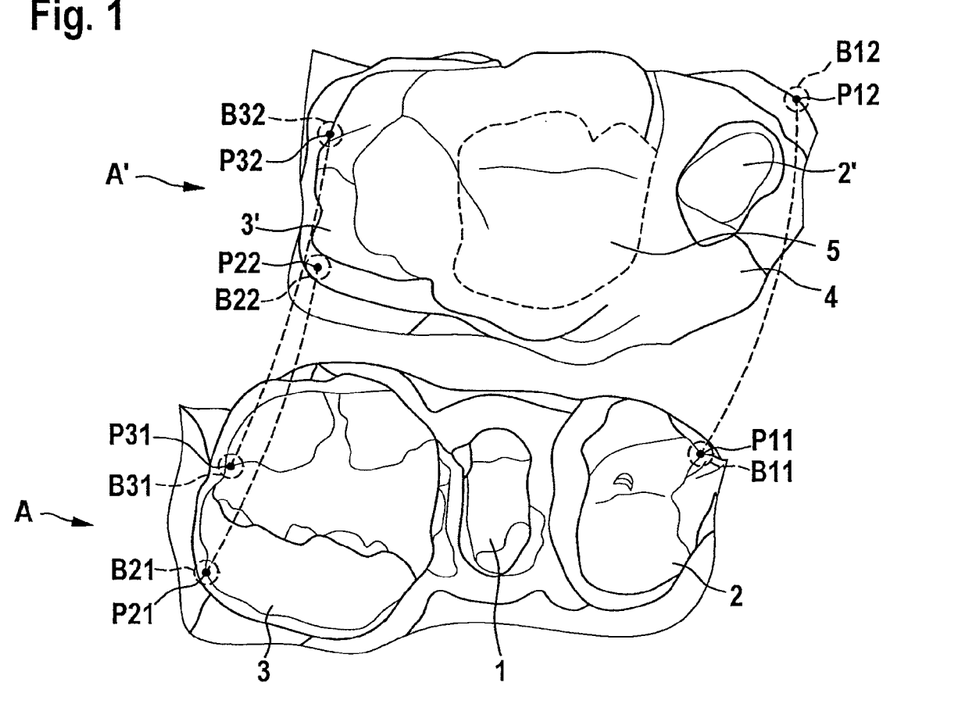
FIG. 1 shows two 3D models A and A'.
Figure 6:
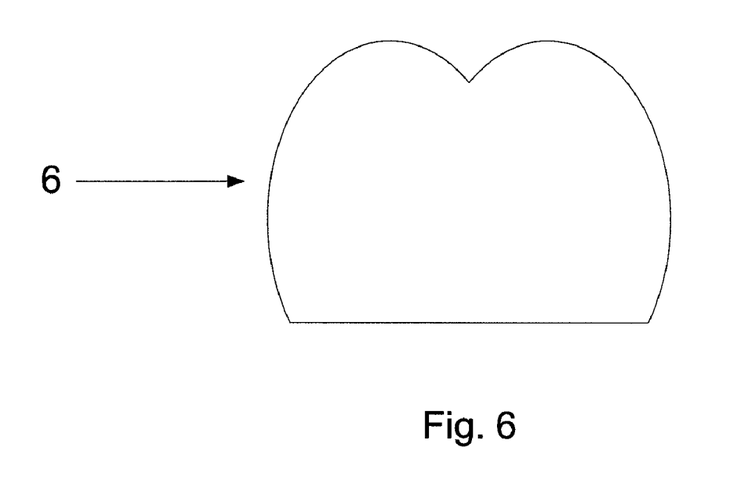
FIG. 6 illustrates an example of a dental prosthetic item, such as a digital dental prosthetic item.

Two 3D models A and A' are shown in FIG. 1. The 3D model A is a digital representation of a prepared tooth 1 with its adjacent teeth 2, 3. The 3D model A' is a data representation in approximately the same preparation site, wherein, however, an impression 5 of the opposite jaw is contained in an impression compound 4 and wherein the adjacent teeth 2', 3' are predominately covered by the impression compound 4. Parts of the impression 5 should be taken into account when designing a dental prosthetic item (such as, e.g., item 6 of FIG. 6), in this case the chewing surface in said impression 5. Up to this point, the two 3D models A, A' do not yet have any spatial relationship to each other. By comparing distinctive surface points or regions, one can see with the naked eye that there are surface points or regions on the surface that correspond to each other in the two models. In particular, the surfaces are edges or crests.

Both of the 3D models A, A' are represented at the same degree of magnification and hence match in terms of their displayed dimensions. In principle, representation of the models on a different scale is also possible, because the regions represented are always based on absolute data.

The operator can therefore define points P11-P32 or regions B11-B32 of adjacent points, which points or regions reproduce the same object parts in the two 3D models A, A', in this case parts of the adjacent teeth 2, 2'; 3, 3'. By marking point pairs P11, P12; P21, P22; P31, P32, wherein in each case one point P11, P21, P31 of a pair lies on the 3D model A and the other point P12, P22, P32 of the pair lies on the 3D model A', a clear positional correlation can be obtained using mathematical methods known in the prior art. This is likewise possible when the representations differ in size.

Figure 2:
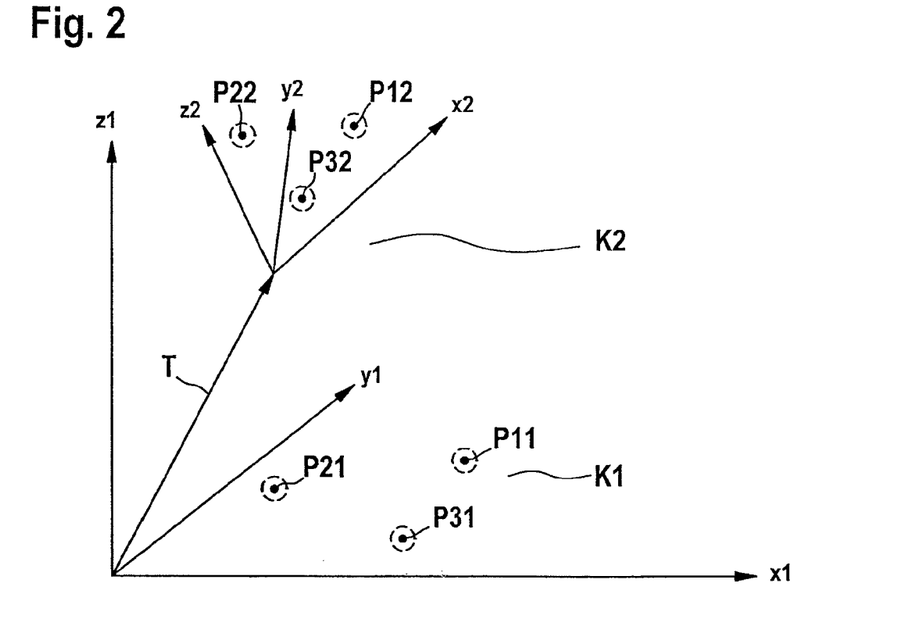
FIG. 2 shows the positional correlation illustrated in abstract form by a first coordinate system K1 and a second coordinate system K2.

In FIG. 2, the positional correlation is illustrated in abstract form by means of a first coordinate system K1 and a second coordinate system K2 and a transformation T for giving the correlation position. Point pairs (P11, P12), (P21, P22) (P31, P32) are selected in both coordinate systems, from which point pairs the transformation T is calculated. The coordinate system K2 may be reproduced therewith on the coordinate system K1 according to the following mathematical formula:

$$K_1 = T * K_2$$

Figure 3A:
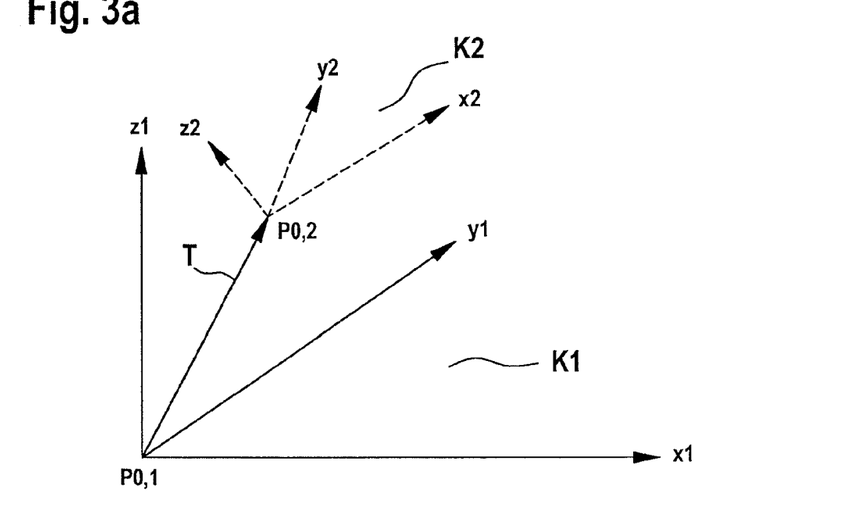
FIG. 3a illustrates another method for obtaining a positional correlation by means of a first step.

Another method for obtaining a positional correlation between the two coordinate systems K1, K2 is illustrated in FIG. 3a. First of all, a first transformation T is calculated with reference to a point pair (P01, P02), which transformation reproduces the point P02 over the point P01 and contains exclusively one translation fraction.

Figure 3B:
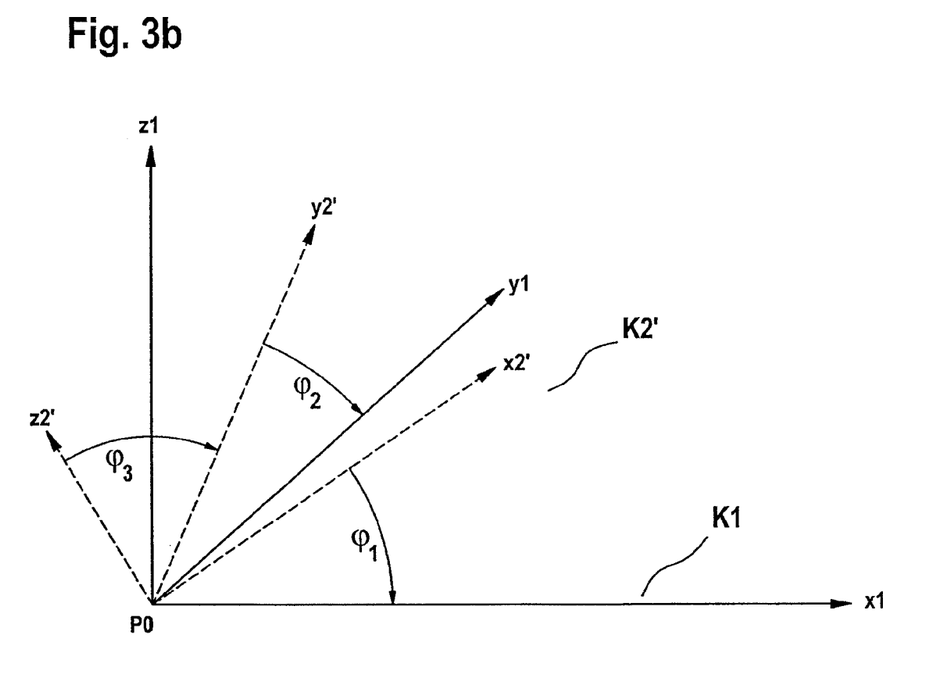

Then a rotation of the coordinate system K2' about the common point P0 through the angles φ1, φ2, φ3 of the axes x, y and z is performed by the operator, as illustrated in FIG. 3b, in order to bring about coincidence of the two coordinate systems K1, K2 in the coordinate system K1. A transformation R is determined therefrom, which transformation contains the angle of rotation only and no translation fraction. Lastly, a positional correlation is calculated for the coordinate systems K1, K2:

$$K_1 = R * (T * K_2)$$

Figure 4:
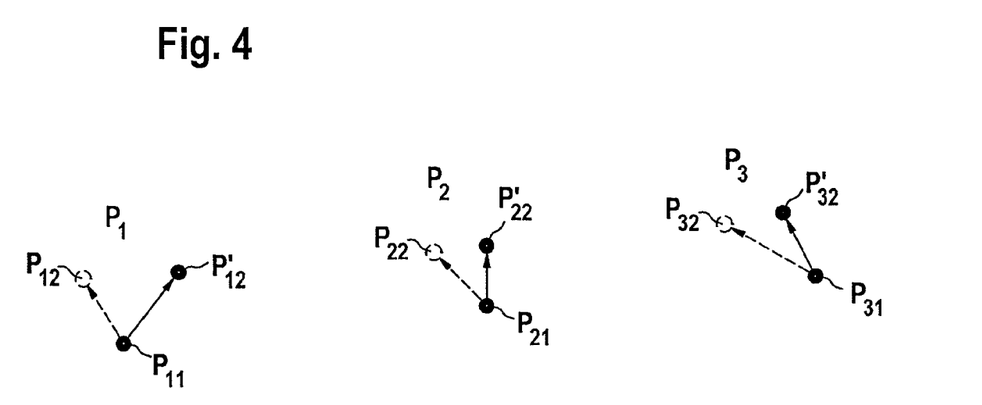
FIG. 4 illustrates a first optimization for determination of the positional correlation.

FIG. 4 illustrates how the positional correlation of the three point pairs P1, P2, P3 is determined. To this end, the transformation is sought in which the three point pairs P1, P2, P3 are disposed relative to each other such that the spacing between the points (P11, P12'), (P21, P22') and (P31, P32') and the points P12', P22' und P32' after the transformation T of the points P12, P22 and P32 of the 3D model A' is minimal. This is accomplished with algorithms known per se using the following formula, in which n=3 in the present case:

$$\min \sum_{i=1}^{n} \|P_{i1} - T \cdot P_{i2}\|$$

As a consequence of the transformation T obtained in this manner, the points P12, P22 and P32 are thus displayed over the points P12', P22' und P32' and the transformation can also be applied to the rest of the 3D model A' in order to obtain the positional correlation of single points or selected regions.

This applies similarly to a region generated from a plurality of points.

Figure 5:
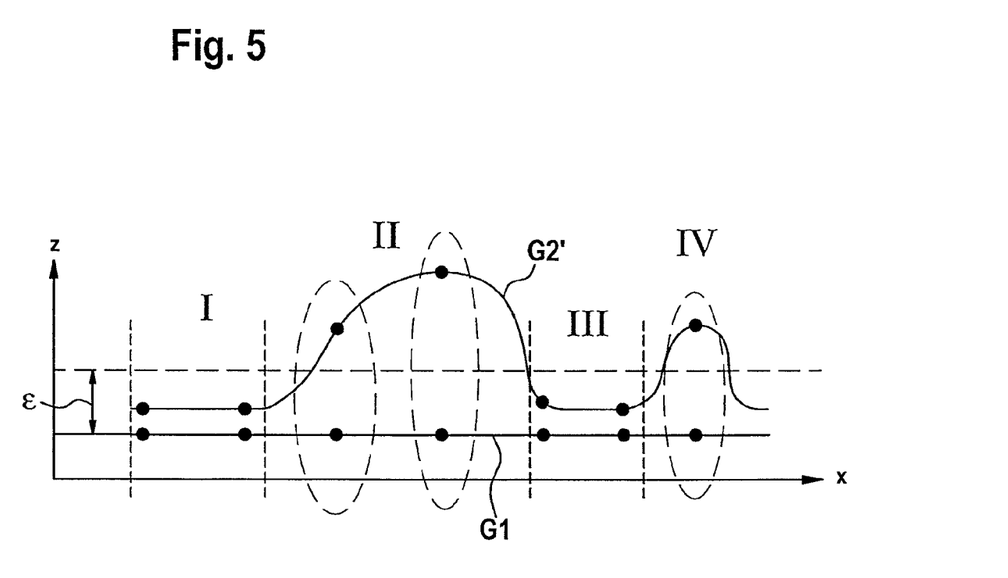
FIG. 5 illustrates another optimization for determination of the positional correlation.

An optimization is illustrated in FIG. 5. Based on the assumption that, after performing the first transformation, image regions with slight changes between the two models will lie close to each other and therefore be spaced at short distances, those regions exceeding predefined maximum spacing will be screened out in order to optimize the transformation.

As an example of the profile of a dental prosthetic item surface as a 3D model, a curve G2' is illustrated together with a curve G1 in the x,z plane from the first coordinate system, which curve G2' was generated from a curve G2 (not shown), from the second coordinate system after the first transformation. The profile of the curve G2' comprises regions I, III, which regions are separated from the curve G1 at intervals within a maximum value ϵ, whereas, by contrast, the deviation is clearly greater than the maximum value ϵ in the regions II and IV. Said regions II and IV are considered as defects and are omitted in the calculation of the final transformation. The positional correlation is therefore only calculated with those values of the regions I and III which lie within the maximum limit ϵ.

Ideally, the curves in regions I and III coincide after this additional transformation.

In order to achieve this good match, it is self-explanatory that the point pairs for the first transformation should fall within the regions I and III.

We claim:

1. A method for designing at least one tooth surface of a digital dental prosthetic item existing as a 3D data set using a first 3D model of at least one of a preparation site and the digital dental prosthetic item, and a second 3D model, the second 3D model including regions which match at least some regions on the first 3D model and non-matching regions which differ from at least some other regions of said first 3D model, the non-matching regions containing at least some surface information required for the digital dental prosthetic item, the method comprising:

selecting at least three pairs of points corresponding to each other on the first and second 3D models, wherein the at least three pairs are selected on at least one of matching regions of the first 3D model and the second 3D model, such that (1) a positional correlation of said second 3D model with reference to said first 3D model is determined with reference to said at least three pairs, (2) a sum of distances of the points on the first 3D model from the points on the second 3D model is minimized for the purpose of determining the positional correlation, and (3) portions of non-matching regions of said first and second 3D models are implemented for designing the at least one tooth surface of the digital dental prosthetic item taking into consideration the positional correlation.

2. A method for designing at least one tooth surface of a digital dental prosthetic item existing as a 3D data set using a first 3D model of at least one of a preparation site and the digital dental prosthetic item, and a second 3D model, the second 3D model including regions which match at least some regions on the first 3D model and non-matching regions which differ from at least some other regions of said first 3D model, the non-matching regions containing at least some surface information required for the digital dental prosthetic item, the method comprising:

selecting a plurality of points on at least one of matching regions of the first 3D model and the second 3D model, such that (1) a positional correlation of at least one matching region of said second 3D model with reference to the first 3D model is determined with reference to said plurality of points, (2) a sum of distances of regions of the first 3D model from the regions of the second 3D model is minimized for the purpose of determining the positional correlation, and (3) portions of the non-matching regions of said first and second 3D models are implemented for designing the at least one tooth surface of the digital dental prosthetic item taking into consideration the positional correlation.

3. A method as defined in claim 2, further comprising determining a plurality of regions having a plurality of points.

4. A method for designing at least one tooth surface of a digital dental prosthetic item existing as a 3D data set using a first 3D model of at least one of a preparation site and the digital dental prosthetic item and a second 3D model, the second 3D model including regions which match at least some regions on the first 3D model and non-matching regions which differ from at least some other regions of said first 3D model, the non-matching regions containing at least some surface information required for the digital dental prosthetic item, the method comprising:

selecting a pair of points corresponding to each other on matching regions on said first 3D model and said second 3D model;

moving said second 3D model in a display so as to coincide with said first 3D model at at least one of the points;

adjusting said second 3D model about the at least one point relatively to said first 3D model to form an adjusted model;

determining a positional correlation with reference to the adjusted model, the determining including minimizing a sum of a distance between the pair of points; and implementing at least some of the non-matching regions of the first and second 3D models for designing the at least one tooth surface of the digital dental prosthetic item taking into consideration the positional correlation.

5. A method as defined in claim 1, wherein the positional correlation is determined based on a result of performing a transformation.

6. A method for designing at least one tooth surface of a digital dental prosthetic item existing as a 3D data set using a first 3D model of at least one of a preparation site and the digital dental prosthetic item, and a second 3D model, the second 3D model including regions which match at least some regions on the first 3D model and non-matching regions which differ from at least some other regions of said first 3D model, the non-matching regions containing at least some surface information required for the digital dental prosthetic item, the method comprising:

selecting at least three pairs of points corresponding to each other on the first and second 3D models,     wherein the at least three pairs are selected on at least one of matching regions of the first 3D model and the second 3D model, such that (1) a positional correlation of said second 3D model with reference to said first 3D model is determined with reference to said at least three pairs, and (2) portions of non-matching regions of said first and second 3D models are implemented for designing the at least one tooth surface of the digital dental prosthetic item taking into consideration the positional correlation;

determining a first transformation with reference to at least one of the pairs of points; and     using those ones of the regions, which, following execution of the first transformation, show a smaller difference in height than a specified maximum value ($\epsilon$) between said first 3D model and said second 3D model as the basis for determination of an additional positional correlation.

7. A method as defined in claim 6, further comprising performing a second transformation.

8. A method as defined in claim 1, wherein the preparation site includes at least one dental structure.

9. A method as defined in claim 8, wherein the second 3D model is a model of a material having an impression of the at least one dental structure.

10. A method as defined in claim 2, wherein the preparation site includes at least one dental structure.

11. A method as defined in claim 10, wherein the second 3D model is a model of a material having an impression of the at least one dental structure.

12. A method as defined in claim 4, wherein the preparation site includes at least one dental structure.

13. A method as defined in claim 12, wherein the second 3D model is a model of a material having an impression of the at least one dental structure.

14. A method as defined in claim 6, wherein the preparation site includes at least one dental structure.

15. A method as defined in claim 14, wherein the second 3D model is a model of a material having an impression of the at least one dental structure.

* * * * *

UNITED STATES PATENT AND TRADEMARK OFFICE
CERTIFICATE OF CORRECTION

PATENT NO.       : 7,796,811 B2
APPLICATION NO.  : 11/368535
DATED            : September 14, 2010
INVENTOR(S)      : Ulrich Orth et al.

It is certified that error appears in the above-identified patent and that said Letters Patent is hereby corrected as shown below:

ON COVER PAGE AT (73) ASSIGNEE

"Benshiem (DE)" should read --Bensheim (DE)--.

Signed and Sealed this

Thirtieth Day of November, 2010

David J. Kappos
*Director of the United States Patent and Trademark Office*